United States Patent [19]
Rolf

[11] Patent Number: 5,804,213
[45] Date of Patent: Sep. 8, 1998

[54] BIOLOGICALLY ACTIVE AQUEOUS GEL WOUND DRESSING

[75] Inventor: David Rolf, Minneapolis, Minn.

[73] Assignee: LecTec Corporation, Minnetonka, Minn.

[21] Appl. No.: 914,751

[22] Filed: Jul. 15, 1992

Related U.S. Application Data

[63] Continuation-in-part of Ser. No. 774,064, Oct. 9, 1991, abandoned.

[51] Int. Cl.$^6$ ............................... A61F 13/00; A61K 9/00
[52] U.S. Cl. .............. 424/445; 424/495.1; 424/DIG. 13; 424/94.1; 424/698; 424/443; 424/444; 514/928; 514/2
[58] Field of Search ..................................... 424/443, 445, 424/447, 195.1, DIG. 13, 698, 94.1; 426/108; 514/2, 928

[56] References Cited

U.S. PATENT DOCUMENTS

| | | | |
|---|---|---|---|
| 2,249,536 | 7/1941 | McDowell | 252/316 |
| 2,249,537 | 7/1941 | McDowell | 252/316 |
| 2,249,538 | 7/1941 | McDowell | 252/316 |
| 2,441,729 | 5/1948 | Steiner | 99/131 |
| 2,477,861 | 8/1949 | Clark et al. | 260/209.6 |
| 2,653,610 | 9/1953 | Smith | 128/272 |
| 2,653,611 | 9/1953 | Smith | 128/272 |
| 2,741,559 | 4/1956 | Banowitz | 99/171 |
| 2,756,874 | 7/1956 | Erickson | 206/47 |
| 3,008,835 | 11/1961 | Madding | 99/171 |
| 3,207,420 | 9/1965 | Navarrete-Kindelan | 229/56 |
| 3,251,781 | 5/1966 | Jordan | 252/316 |

(List continued on next page.)

FOREIGN PATENT DOCUMENTS

| | | |
|---|---|---|
| 0302536 | 2/1989 | European Pat. Off. . |
| 0405993 | 1/1991 | European Pat. Off. ......... A61L 15/60 |
| 77123602 | 5/1979 | Sweden .......... A61L 15/01 |
| 2182663 | 11/1985 | United Kingdom ............. C08J 9/00 |
| 2194144 | 3/1988 | United Kingdom . |
| 2229443 | 9/1990 | United Kingdom ................... 424/445 |

OTHER PUBLICATIONS

"Current and Future Trends in Wound Management 2: Modern Surgical Dressings" Pharmacy International Jun. 1985, pp. 131–134.

"Wound Dressings" Pharmacy Update, Apr. 1987, pp. 147–150.

Journal Article: "Time Course of Wound Healing" *Journal of Biomaterials Applications*, vol. 5, Apr. 1991, pp. 337–362.

Journal Article: "Growth Factors for Wound Healing—An Overview" *Medical Marketing & Media*, Oct. 1990, pp. 54–63.

*Primary Examiner*—Raj Bawa
*Attorney, Agent, or Firm*—James V. Harmon

[57] ABSTRACT

The invention provides a prepackaged dressing including dry particulate solids for forming a pourable, water-based natural or synthetic hydrocolloidal polymeric gel to dress wounds. The gel contains a biologically active constituent. Liquid and dry, solid particulate components are separate and are mixed just before use. One dry constituent is the hydrocolloid which is contained in a compartment of a sealed container separate from moisture. After mixing with water, the dry hydrocolloid does not become fully hydrated immediately. The liquid component (water) provides a fluid consistency initially. At this stage, the admixture is sufficiently fluid in consistency to allow it to be poured or spread into a wound. Following application to the wound, the hydrated hydrocolloidal dispersion begins to solidify to form a solid, self-supporting flexible dressing structure consisting primarily of water, the hydrocolloid, as well as the biologically active constituent, e.g., an antibiotic, disinfectant, growth factor or the like in contact with the tissue of the animal or human patient. A gelling or cross-linking agent can also be used advantageously with some of the hydrocolloids. The resulting dressing becomes molded to the shape of the wound and contains a large quantity of moisture that will maintain the wound in a moist condition.

14 Claims, 2 Drawing Sheets

U.S. PATENT DOCUMENTS

| | | | |
|---|---|---|---|
| 3,265,631 | 8/1966 | Jordan | 252/316 |
| 3,293,048 | 12/1966 | Kutterman | 99/171 |
| 3,301,723 | 1/1967 | Chrisp | 149/20 |
| 3,550,592 | 12/1970 | Bernardin | 128/290 |
| 3,637,132 | 1/1972 | Gray | 229/53 |
| 3,972,328 | 8/1976 | Chen | 128/156 |
| 4,071,467 | 1/1978 | Nordgren | 252/316 |
| 4,090,013 | 5/1978 | Ganslaw et al. | 526/15 |
| 4,333,461 | 6/1982 | Muller | 128/284 |
| 4,393,048 | 7/1983 | Mason, Jr. | 424/132 |
| 4,410,321 | 10/1983 | Pearson et al. | 604/56 |
| 4,550,825 | 11/1985 | Sutryn et al. | 206/222 |
| 4,563,174 | 1/1986 | Dupont et al. | 604/89 |
| 4,596,713 | 6/1986 | Burdette | 426/107 |
| 4,613,497 | 9/1986 | Chavkin | 424/44 |
| 4,617,326 | 10/1986 | Björnberg et al. | 523/111 |
| 4,624,868 | 11/1986 | Muller | 427/384 |
| 4,693,713 | 9/1987 | Chmelir et al. | 604/368 |
| 4,770,295 | 9/1988 | Carveth et al. | 206/219 |
| 4,948,575 | 8/1990 | Cole | 424/445 |
| 5,089,606 | 2/1992 | Cole et al. | 536/54 |

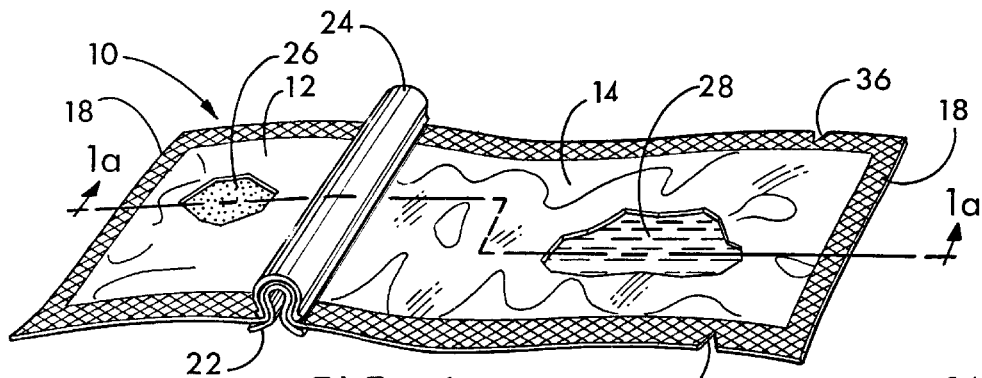
FIG. 1
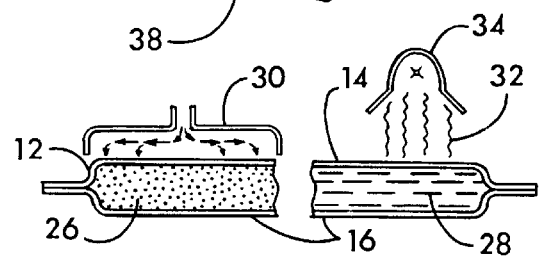
FIG 1a
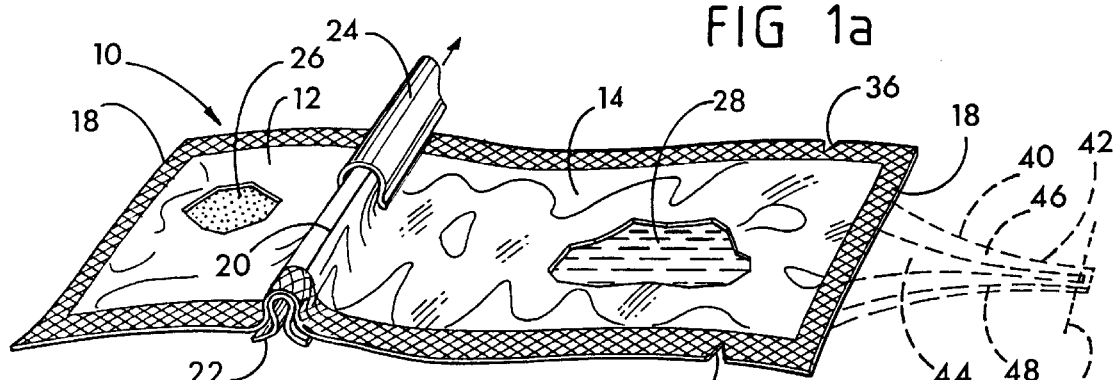
FIG. 2
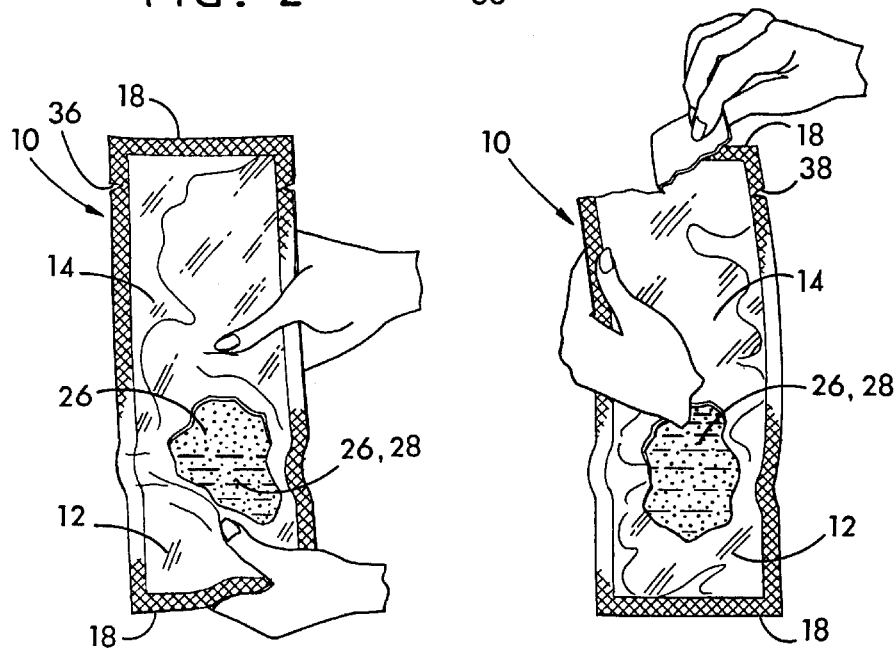
FIG. 3
FIG. 4

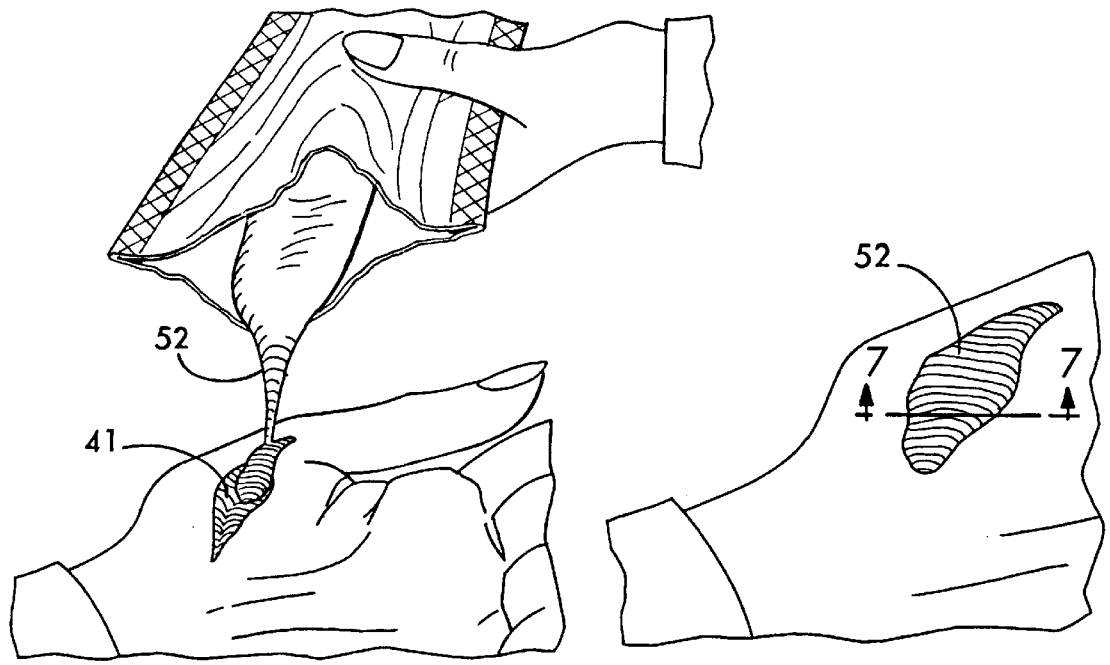
FIG. 5
FIG. 6
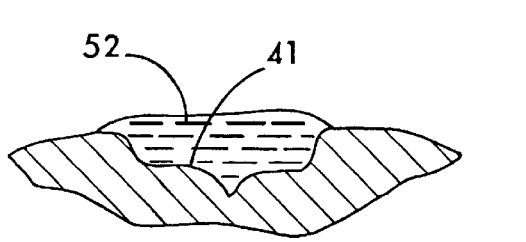
FIG. 7
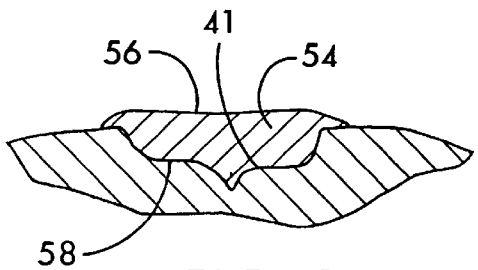
FIG. 8
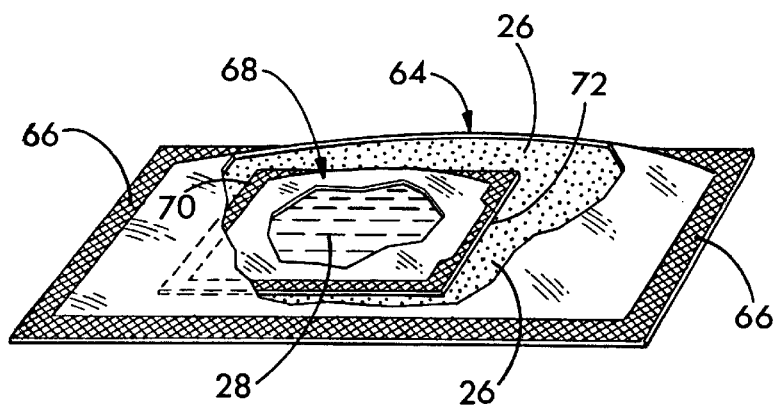
FIG. 9

BIOLOGICALLY ACTIVE AQUEOUS GEL WOUND DRESSING

The present application is a continuation-in-part of my prior application Ser. No. 07/774,064, filed Oct. 9, 1991, abandoned, and entitled AQUEOUS GEL AND PACKAGE FOR A WOUND DRESSING AND METHOD.

FIELD OF THE INVENTION

The invention relates to an aqueous gel for dressing wounds which contains a biologically active constituent as well as to a package for mixing solid and aqueous components and to a method of preparing the biologically active dressing for application to a wound.

BACKGROUND OF THE INVENTION

The healing of wounds, such as wounds resulting from injury, surgical wounds or decubitus ulcers, is greatly dependent upon the dressing used. Conventional bandages often do not provide optimum results. In the case of a decubitus ulcer, treatment should include the removal of necrotic tissue and the establishment of an environment that enhances wound healing. Special pressure-relieving or reducing measures should also be taken. A moist dressing is often beneficial. Some of the advantages of a moist wound dressing are the rehydration of dehydrated tissue; increased angiogenesis, i.e., proliferation of new blood vessels; minimized bacterial growth; physical protection; and the maintenance of the proper pH for stimulating the release of oxygen and for allowing proteolytic enzymes to work more efficiently.

In the past, starches in granular form have been applied to wounds and dextrans have been applied as beads or as a paste. Calcium alginates have also been applied to wounds in powdered or granular form. These prior products have certain disadvantages. Powder or granules cannot be applied evenly. Consequently, they do not absorb tissue moisture evenly, causing nonhomogeneous hydration or swelling of the dry granules. Pastes must be spread onto the tissue. Generally speaking, granular absorbent dressings are difficult to remove completely from the wound bed. Dressing changes typically require irrigation of the wound bed to remove the gel granules. The pressure required to spread the paste can be painful or further traumatize the tissue. In addition, an even application is not always easy to achieve because the product retains its plastic character. If made part of a cloth bandage, the dressing may not have intimate contact with the tissue. In the case of a powder, sterility may be difficult to maintain because air containing airborne pathogens will enter the package, replacing and contaminating the powdered product as it is poured from the container.

British patent GB 2 229 443A describes a two component wound dressing that is a mixture of a gel-forming component together with a film forming component. This mixture forms a coherent film over the wound. The composition has to be kept refrigerated prior to use (pg. 3, lines 1–6). The gel former comprises block copolymers of polyoxyethylene-polyoxypropylene sold under the name Pluronic. The film formers comprise hydroxyethylcellulose, hydroxypropylmethylcellulose or polyvinyl alcohol. Unlike the present invention, these compositions have reversible thermosetting gel properties and have to be kept refrigerated prior to use (pg. 11, lines 14–15). The composition experiences a reversible temperature controlled liquid/gel transition at a temperature range of 16° C. to 20° C. By contrast, the present invention does not revert to a liquid upon heating or cooling and requires no film former, only a gel former. In tests conducted with the composition of the present invention through a range of 13° C. to 33° C., the gel was found to remain elastic but nonfluid, i.e., in a gelled condition and thus is a solid that is temperature non-reversible. This was shown by appyling pressure to the surface of the gel with an instrument. As pressure is increased, the gel will deform and eventually fracture rather than flow around the instrument. Moreover, the hydrocolloid composition of the present invention is stored dry and is mixed with water just before use, preferably under sterile conditions, forming a dispersion which is initially fluid but which sets up without the necessity of a temperature change. The present invention does not contain a film former comprising a cellulose derivative or polyvinyl alcohol.

The invention also includes a biologically active constituent, such as a coagulant, antibiotic, disinfectant, growth factor or other biologically active substance to be described more fully hereinbelow.

In view of these and other deficiencies of the prior art, it is a major objective of the invention to provide a sterile wound dressing and package enabling the dressing to be prepared from two components and which is initially fluid to facilitate application to the wound but which, after being applied, will form a stable, elastic gel in situ to protect the wound and maintain a moist environment at the tissue surface. Another object is to provide a dressing that is shelf stable yet is easily prepared and requires no refrigeration. Another object is to provide a gel for dressing wounds that holds its shape through a wide range of temperatures, i.e., that forms a solid that is temperature non-reversible, and can be removed from the wound bed in a solid plug. Still another object is to provide a dressing that will conform to the exact shape of the wound. The term "wound" herein includes burn injuries. Yet another object is to provide a package that protects the dressing product, facilitates mixing and allows precise application to the wound. A further object is to provide a moist, initially fluid wound dressing which sets up in situ shortly after being applied, contains a quantity of moisture and, optionally, one or more medications or disinfectants to promote healing.

When biologically active preparations are applied to a wound in a dry state, absorption is reduced and tends to be spotty. However, if diluted with water, the biologically active preparation can flow away from the point where it was applied. It is therefore a general object to apply a biologically active agent to a wound in a manner that will ensure uniform and continuous delivery of the biologically active agent to the wound and will provide the agent to the tissue interface in its most active form. Another more specific object is to provide means through which a gel dressing provides a biologically active function. Still another object is to provide the biologically active agent in a form that has excellent storage characteristics and will therefore maintain its biological activity when stored for long periods of time.

These and other more detailed and specific objects of the present invention will be apparent in view of the following description setting forth by way of example but a few of the various forms of the invention that will be apparent to those skilled in the art once the principles described herein are understood.

THE FIGURES

FIG. 1 is a perspective view illustrating one form of package used in accordance with the invention;

FIG. 1A is a semi-diagrammatic cross-sectional view taken on line 1A—1A of FIG. 1 showing sterilization of the package;

FIG. 2 is a view similar to FIG. 1 of an optional, modified form of the package with a clip partially removed;

FIG. 3 is a view of the package of FIG. 1 on a smaller scale illustrating the mixing of its contents;

FIG. 4 is similar to FIG. 3 but shows the package being opened;

FIG. 5 illustrates the application of the dressing to a wound;

FIG. 6 illustrates the dressing after being applied to the wound;

FIG. 7 is a vertical cross-sectional view taken on line 7—7 of FIG. 6 while the dressing is still fluid;

FIG. 8 is a view similar to FIG. 7 after the dressing has solidified to form a self-supporting gel; and FIG. 9 shows a modified form of package.

SUMMARY OF THE INVENTION

The invention provides a prepackaged wound dressing comprising a natural or synthetic hydrocolloid in dry particulate form. A source of a measured quantity of water and a biologically active agent are also provided. These constituents are mixed just before use to form a briefly pourable, water-based natural or synthetic water soluble or water swellable hydrocolloidal polymeric gel for dressing wounds. Just after mixing, the gel is initially sufficiently fluid to be poured or spread into a wound but after application it forms a moist, solid elastic protective gel that contains the natural or synthetic polymeric hydrocolloid in a hydrated state. A biologically active agent is dispersed in the gel. The separate liquid and solid components are preferably contained in separate sealed compartments of the same sealed container for being mixed together just before use. Just after mixing, the liquid component (water) gives the dispersion a fluid consistency initially, allowing it to be poured or spread into or onto the wound and to be precisely applied in the exact quantity and to the precise location required. The dispersion then solidifies to form a solid but elastic and pliable, self-supporting moist dressing structure which holds the biologically active agent in contact with the wound.

Water can be provided as one component of the package or, if desired, any available source of water can be used provided it is maintained in a sterile condition when mixed with the dry hydrocolloid. However, to best assure that the entire composition is sterile prior to application and that the correct amount of water is used, it is preferred to provide the required water in either the same container as the solid ingredients or in a companion container which can be easily mixed with the solid constituents under sterile conditions. The resulting dressing sets up on or within the wound so as to become molded to the shape of the wound and contains a large quantity of moisture that will maintain the wound in a moist condition.

DETAILED DESCRIPTION OF THE INVENTION

In a preferred form of the invention, both solid and liquid constituents, typically a dry hydrocolloid polymer in particulate form, water and a biologically active agent, are prepackaged in a container having at least two separate compartments. The water is separate from the dry hydrocolloid polymer. The invention facilitates mixing of these constituents under sterile conditions while still enclosed in the same package provided for shipping and storing the product. It is also preferred that a portion of the package be removed to enable the initially fluid gel, which is in a pourable condition, to be easily expelled onto the wound. The hydration of the dry particulate hydrocolloid begins the moment the solid and liquid constituents come in contact with each other, i.e., upon mixing. The product, a dispersion, is, however, liquid at this stage and therefore can be easily applied to cover or fill a wound of any shape. As soon as it is applied, the dressing occupies the void within a wound. The lower surface of the dressing has the same contour as the wound itself, i.e., the wound serves as a mold for shaping the dressing which then begins to solidify into a solid but flexible, three-dimensional form. The gel thus formed in the wound is also strong enough to allow for easy removal and to provide some cushioning for the wound bed, i.e., protecting the wound. Besides maintaining a moist wound surface, the dressing also absorbs exudate from the wound and supplies the biologically active agent to the tissue.

In a typical application, the freshly mixed solid and liquid components will remain fluid and pourable for about 10 second to 3 minutes. The fresh mixture typically has a viscosity of less than 6,000,000 cp at the beginning. At higher temperatures, the composition tends to solidify more rapidly. For example, at 34° C., a typical composition of the present invention reaches 6 million centipois in about 25 minutes, whereas at 15° C. it takes an hour. Other factors that affect the length of time that the dispersion remains as a fluid and the ultimate strength of the gel include the chemical composition of the polymer and cross-linker, if any, as well as the concentration of each. It is highly preferred that the liquid dispersion have sufficient body or viscosity to allow the wound to be filled with little or no tendency to flow out of or away from the wound; i.e., it is preferred that the dressing is not watery enough to flow or drip from the wound.

The term "gel" herein refers to a solid or semi-solid, elastic, pliable substance formed by the solidification of an aqueous colloidal disperson. The term "fluid" refers to a water-based hydrocolloidal composition that has sufficient liquidity to be poured or spread onto a wound. The chemical composition of the natural or synthetic hydrocolloidal polymer employed should be selected to form a gel spontaneously after hydration or, if desired, the hydrocolloid can be one requiring a cross-linking agent to induce or enhance solidification of the polymer. The present invention encompasses both of these systems.

The unique wound dressing of the present invention is easy to ship and mix. It is also easy to apply and use. It is supple, elastic, pliable, soft, semi-solid and conforms naturally to the contours of the wound. The water in the dressing keeps the wound moist. The dressing is non-irritating, has no odor and promotes healing. The dressing will remain in place after application but can be easily removed when required.

The invention is illustrated by way of example in FIGS. 1–8. Shown in FIGS. 1–8 is a receptacle or container 10, in this case a pouch formed from flexible sheet material including upper and lower sheets, in this case consisting of an upper sheet of paper 12, an upper sheet of plastic 14 and a lower sheet of plastic 16. The sheets are sealed together at their edges, e.g., by means of heat and pressure (a heat seal) to form a peripheral fin seal 18 which extends around the entire container 10. The paper sheet 12 is sealed to the plastic sheet 14 along a transverse seal line 20. Communication inside the container 10 on either side of the seal line 20 is prevented by means of a barrier, in this case a pair of inter-fitting inner and outer plastic C-shaped clips or channels 22 and 24, respectively, which are placed on opposite sides of the pouch 10 at the seal line 20 and snapped together with the pouch 10 pressed between them and forming a sharp bend in the pouch 10 over the inner clip 22. In this way, two separate compartments are formed, preventing contact between dry powder constituents 26 and liquid constituents 28 (water). The package 10 is shipped as shown in FIG. 1 with the water solution 28 separated from the dry particulate gel-forming hydrocolloid polymer 26 together with other desired ingredients such as dry cross-linking agents which at this stage are inactive. Biologically active agents are mixed either with the dry hydrocolloid polymer or with the water.

The package containing liquid and solid constituents 28, 26 is preferably sterilized. In this case, the contents are sterilized as shown in FIG. 1A. The paper sheet 12 is porous, allowing a sterilizing gas such as ethylene oxide to be introduced into the pouch 10 to the left of the barrier 22, 24, e.g. through a gas applicator manifold 30. The paper 12 is also impervious to pathogenic organisms. Exposure to ethylene oxide for a period of 360 minutes has been found satisfactory. To the right of the barrier 22, 24 the liquid constituents 28 are sterilized by being exposed to ionizing radiation 32 from a gamma radiation source 34 of ≧2.5 Mrad. The ionizing radiation should be used to sterilize the water or aqueous solution prior to adding the dry particulates to the pouch.

The paper sheet 12 can be 37.5-pound per ream porous, waterproof paper, e.g., Tyvek® paper (available from DuPont, Inc. of Wilmington, Del.), and the plastic sheets 14, 16 can be a 5 mil laminate, e.g. of polyethylene, aluminum foil, polyethylene and Mylar® as available from Technipaq Corporation of Chicago, Ill. Indentations 36, 38 can can be provided at one end of the pouch to facilitate opening. In the alternative, as shown in FIG. 2, the pouch 10 can be provided with an extension 40 at one end which narrows to form a pointed dispensing point 42 containing a central duct 44 between edge seals 46 and 48. The dispensing point 42 can be cut with a scissors at 50 to provide a pointed spout through which the contents can be expelled when desired.

To use the package 10, the clips 22, 24 are removed by sliding portion 24 away from portion 22 as shown in FIG. 2. This allows communication between solid and liquid ingredients 26 and 28, respectively. Mixing of solid and liquid ingredients is accomplished manually as shown in FIG. 3, for about one minute until a homogeneous slurry is produced.

As shown in FIG. 4, the end portion of the package 10 above the indentations 36, 38 is then removed. At this stage the aqueous hydrocolloid dispersion is a liquid and preferably sufficiently fluid to allow it to be poured into the wound as shown in FIG. 5. The dry solid constituents 26 begin to hydrate the moment the solid and liquid contact each other. After mixing, the mixture will remain fluid and pourable for typically about 10 seconds to 3 minutes. During this time, while the hydrocolloid dispersion is fluid, it will typically have a viscosity of less than 6,000,000 cp (Brookfield). It should at least be sufficiently fluid to allow it to be easily spread onto the wound, e.g. with a spatula. However, pouring is preferred.

It will be noticed that the liquid hydrocolloid mixture 52, as it is poured from the package 10 into the wound 41, will form a three-dimensional body substantially filling the wound; in other words, having a lower surface which conforms exactly to the shape of the wound. The hydrocolloid is in effect molded by the contour of the wound. Within a short time after application, typically five to ten minutes, the liquid hydrocolloid 52 solidifies to form a three-dimensional, self-supporting solid but elastic dressing body 54 with a substantially flat or slightly upwardly curved upper surface 56 and a lower surface 58 which conforms to the lower surface of the wound 41.

The combination of gas pervious and gas impervious materials in a single container has highly beneficial and unique properties, allowing a liquid to be held on one side of the barrier 22, 24 and a dry ingredient on the other side but both can be efficiently sterilized while in the same package. In this way, the package 10 provides for two kinds of sterilization in a single package. This is accomplished by providing two distinct components; paper 12 and plastic 14, 16. This eliminates the need for filling the package under sterile conditions which can substantially complicate and increase the cost of assembling packages. Thus, the invention provides the ability to mix two separate sterile components just before use. A sterile dressing can thus be delivered to a wound whenever needed with no requirement for refrigeration.

The invention can be applied to all kinds of wounds, including abrasions which are flat, but it is particularly useful in filling a wound which has a cavity or uneven surface. The unique wound dressing body 54 is easy to apply and use. The dressing 54 is supple, pliable, soft, solid but elastic, and conforms exactly to the contours of the wound 41. The moisture in the dressing 54 facilitates healing. The dressing is non-irritating, has little odor, and promotes healing. The dressing 54 will remain in place after being applied to the wound 41, but it can be easily removed later when required. Besides maintaining the wound 41 in a moist condition, the dressing 54 will absorb exudate from the wound as well as evaporate moisture from its top surface.

The solid dressing 54 is also non-cytotoxic. Removal of the dressing as a solid plug which is then weighed provides a convenient method of monitoring progress of wound healing. Since it is elastic, the dressing provides a cushioning function for the wound.

Refer now to FIG. 9 which illustrates a package that includes a flexible envelope 64 similar to the envelope 12 sealed along its edges as shown at 66, e.g. by means of a heat seal, and containing the same dry powdered dressing composition 26 as well as a pressure-rupturable envelope 68 containing water in which is dissolved a cross-linking agent when used and sealed along its edges at 70 similar to the envelope 12 but having a rupturable section 72 in which the seal 70 is narrower and hence weaker to provide a sealed vent opening at 72 which will rupture when the envelopes 64 and 68 are pressed between the fingers, thereby expelling the water 28 from envelope 68 into the dry gel-forming hydrocolloid polymer particles 26. Continued manipulation causes the solid and liquid to mix, forming a sterile uniform dispersion which can be expelled onto the wound after the envelope 68 is opened.

The following method is used to form and use the package of FIG. 9. A predetermined quantity of water is sealed in pouch 68 and is then sterilized, e.g., by gamma radiation as described above. The pouch 68 and hydrocolloid particles 26 are then sealed in the envelope 64 which is preferably composed at least in part of a material such as Tyvek® which is permeable to a sterilizing gas. The envelope 64 is then exposed to a sterilizing gas, in this case ethylene oxide as described above. The package is then ready for use.

The hydrocolloid polymer particles employed can be any suitable biocompatible natural or synthetic gel forming hydrocolloid which, when mixed with water, will form a solid temperature non-reversible elastic gel, i.e., flexible hydrogel with or without a cross-linking agent to assist in the formation of a nonfluid dressing. Both the hydrocolloid and the cross-linking agent must, of course, be nontoxic. When boric acid is used as a cross-linking agent, it provides a bacteriostatic effect. Moisture evaporates from the dressing 54, thereby minimizing dimensional changes resulting from wound exudate absorption. Evaporation also cools the gel, which provides a soothing effect for the patient. While constituents can be sterilized before packaging, it is preferred to sterilize them after they are in the package as described above to more reliably ensure sterility.

If the gel forming hydrocolloid polymer is a natural polysaccharide gum, it is preferred that the molecular weight be typically between about 50,000 and 500,000. One preferred natural gum is guar gum in an amount between about 3% and 15% and preferably between 9% and 12%, the balance being water and trace quantities of cross-linker. Another suitable polymer is locust bean gum. Both guar and locust bean gum are polyglucomannan gums. While the quantities of the several components used in the gel composition can be varied widely depending upon the properties employed, at least a sufficient amount of polymer should be provided to give the gel a solid consistency after being allowed to set in contact with the wound. Generally greater amounts of polymer and cross-linking agent provide a more solid dressing. Sufficient water should be present to provide the initial fluidity required for pouring or spreading the composition onto the wound. When a cross-linker is employed, only enough is needed to cause the polymer to solidify. For most applications, the cross-linking agent can be varied from about 0% to 8% by weight and preferably from about 0.1% to about 5.0% by weight, with the balance, e.g., about 80% to 95% by weight, being water. All quantities herein are expressed as percent by weight.

Any suitable nontoxic cross-linking agent of a composition can be used to form a chemical bond between the molecules of the polymer to gel the dispersion 52, forming a solid body. Examples of cross-linking agents for locust bean gum, guar or chemically modified guar are galactose, organic titanate or boric acid.

When the hydrocolloid is a polyglucomannan (e.g., Konjak®), borax can be used as a cross-linking agent. When xanthan gum is used, a suitable cross-linker for xanthan gum is mannose. If locust bean gum is used as the principle hydrocolloid, lactose or other suitable oligosaccharide can be used. The cross-linked polymers loose water solubility as well as any ability to soften in response to temperature changes. Consequently, once solidified, the dressing is non-thermoplastic, i.e., it will not return to a liquid state by heating or cooling. When a cross-linking agent is used in the following examples, it is packaged with the water. However, if desired, it can be packaged with the dry ingredients.

Any of the following kinds of biologically active substances can be included in the composition: medications and disinfectants as well as wound healing enhancers, e.g., a vitamin preparation, blood coagulants for battlefield applications, antiseptic compounds, antibiotic compounds, or a source of oxygen. Among other biologically active substances are astringents, antibiotics, oxidants, proteolytic enzymes, collagen cross-link inhibitors such as natural or synthetic diamines, e.g., cystamine or histadine, putrescine, spermidine, cadaverine, alpha, omega diamino polyethylene or polypropylene oxide (available as Jeffamine® from Texaco Chemical, Houston, Tex.) and the like, various growth factors, amino acids, macrophage stimulating factors, narcotic analgesics, anesthetics, and the like.

The moisture containing hydrogel can also be formed into an implantable delivery device having the form of a rod, disc or other convenient shape and implanted under the skin through an incision made for that purpose. In this application, the gel is formed from a pharmaceutical grade hydrocolloid, such as a pharmaceutical grade guar gum which has the property of providing a low endotoxin content. One or more of the biologically active agents is incorporated into the liquid gel. In forming an implantable delivery device, the freshly prepared liquid gel is poured into a mold to form the implantable delivery unit containing a biologically active agent. The molded unit, e.g., having a rod form, is then implanted through an incision beneath the skin where it serves as an errodable implanted delivery device for delivering the biologically active composition into the bloodstream of the animal or human patient.

While some of the biologically active agents that are listed in examples 44–69 are stable in a liquid or semi-solid gel matrix, most of the biologically active ingredients exhibit their best stability when stored in dry solid state mixed with the dry hydrocolloid which is in particulate form. This is especially true for enzymatic and proteinaceous molecules such as growth factors, some immunostimulators and proteolytic enzymes. The present wound dressing exhibits a great advantage over ordinary dressings since the dressing of the present invention will permit the storage of relatively unstable biologically active molecules in a solid (freeze dried) state. Freeze drying of biologically active agents (lyophilization) is a common method of preserving many unstable biologically active molecules. Mixing the dried, e.g., freeze dried biologically active agent with liquid components just prior to use in accordance with the present invention will ensure the longest useful lifetime for the biologically active molecules and the resulting gel will hold the biologically active agent in contact with the tissue.

The invention will be better understood by reference to the following additional examples of some of the typical hydrocolloid compositions that can be employed in accordance with the invention. Quantities given are expressed as percent by weight. All quantities in units/g or mg/g refer to grams of the hydrated gel dressing. In all formulations, liquid and solid particulate components are stored separately and are mixed just before use at approximately room temperature (23° C.). Unless otherwise stated, before use the boric acid, borax or other cross-linking agent is present in solution in the water portion of the formula.

EXAMPLES

| Ingredient | % by Weight | Comments |
|---|---|---|
| 1 | | |
| Hydroxy propyl guar* | 9.0 | Dressing thickened |
| Boric acid | 4.4 | very slowly, about |
| Borax | 0.6 | 5 minutes |
| Water | 86.0 | pH = 6.2 |

*Galactasol 418 ®, a hydroxy propyl quar manufactured by the Agualon Company of Wilmington, Delaware. The hydroxy propyl group can be linked to either the galactose or mannose base of the guar molecule.

| Ingredient | % by Weight | Comments |
|---|---|---|
| 2 | | |
| Hydroxy propyl guar | 9.0 | Liquid phase |
| Boric acid | 4.5 | lasted less |
| Borax | 0.5 | than ten seconds. |
| Water | 86.0 | pH = 6.2 |

-continued

| Ingredient | % by Weight | Comments |
|---|---|---|
| 3 | | |
| Hydroxy propyl guar | 10.0 | Crosslinks slowly, |
| Borid acid | 4.2 | somewhat brittle |
| Borax | 0.8 | gel. |
| Water | 85.0 | pH = 6.5 |
| 4 | | |
| Guar (Supercol ®) | 10.0 | Short liquid |
| Water | 90.0 | phase, weak gel. |
| 5 | | |
| Boric acid | 3.6 | Very short liquid |
| Borax | 0.4 | phase, nice gel. |
| Guar (Supercol ®) | 5.0 | |
| Water | 87.0 | |
| 6 | | |
| Boric acid | 1.7 | Very short liquid |
| Borax | 0.3 | phase, chunky |
| Guar (Supercol ®) | 8.0 | gel. |
| Water | 90.0 | |
| 7 | | |
| Cationic guar | 9.0 | Long liquid phase |
| Boric acid | 4.0 | and a soft gel. |
| Water | 87.0 | pH = 6.0 |
| 8 | | |
| Cationic guar | 10.0 | Hardened slightly |
| Boric acid | 5.0 | faster than |
| Water | 85.00 | example #7. |
| | | pH = 5.4 |
| 9 | | |
| Hydroxy propyl guar* | 11.0 | very slow gel |
| Dihydroxy aluminum sodium carbonate (DHSC) | 1.0 | formation from liquid phase. |
| .9% saline (NaCl) | 88.0 | |
| 10 | | |
| Hydroxy propyl guar* | 10.0 | Nice gel within |
| Citric acid | .01 | 10 minutes. |
| .9% saline (NaCl) | 89.0 | pH = 6.7 |
| 11 | | |
| Hydroxy propyl guar* | 10.0 | Slightly weak |
| Boric acid | 1.0 | gel in 10 |
| Citric acid | .01 | minutes. |
| .9% saline (NaCl) | 89.0 | pH = 6.7 |

*Galactasol 418 ®, Aqualon Company of Wilmington, Delaware.

| Ingredient | % by Weight | Comments |
|---|---|---|
| 12 | | |
| Hydroxy propyl guar* | 10.0 | Nice gel in |
| Boric Acid | 1.0 | 5 minutes. |
| Citric acid | 0.1 | pH = 5.8 |
| .9% saline (NaCl) | 89.0 | |

*Galactasol 418 ®, Aqualon Company of Wilmington, Delaware.

| Ingredient | % by Weight | Comments |
|---|---|---|
| 13 | | |
| Hydroxy propyl guar | 10.0 | Lumpy liquid |
| Boric acid | 0.5 | phase lasted |
| Citric acid | 0.05 | less than 15 |
| .9% saline (NaCl) | 89.5 | seconds. |
| | | pH = 6.6 |
| 14 | | |
| Hydroxy propyl guar | 10.0 | Nice gel in |
| Boric acid | 3.0 | 1 minute. |
| .9% saline (NaCl) | 87.0 | |
| 15 | | |
| Hydroxy propyl guar | 11.0 | Gel more brittle |
| Boric acid | 1.0 | than elastic. |
| .9% saline (NaCl) | 88.0 | |
| 16 | | |
| Hydroxy propyl guar | 10.0 | Liquid phase less |
| Boric acid | 1.0 | than 2 minutes; |
| .9% saline (NaCl) | 89.0 | great gel in 30 minutes. |
| | | pH = 6.6 |
| 17 | | |
| Hydroxy propyl guar | 10.0 | Pourable liquid |
| Boric acid | 0.5 | after exactly 1 |
| 9% saline (NaCl) | 89.5 | minute, weak gel. |
| | | pH = 7.0 |
| 18 | | |
| Hydroxy propyl guar | 5.0 | Liquid for 30 |
| Boric acid | 1.0 | seconds, good |
| Guar (Supercol ®) | 5.0 | gel. |
| .9% saline (NaCl) | 89.0 | pH = 6.1 |
| 19 | | |
| Hydroxy propyl guar | 5.0 | Gel formed more |
| Boric acid | 0.5 | slowly than |
| Guar (Supercol ®) | 5.0 | example #18. |
| .9% saline (NaCl) | 89.5 | pH = 6.6 |
| 20 | | |
| Cationic guar* | 5.0 | Two-phase liquid, |
| Boric acid | 1.0. | chunky gel produced rapidly. |
| Guar (Supercol ®) | 5.0 | |
| .9% saline (NaCl) | 89.0 | pH = 6.9 |

*Enhance ®, Aqualon Company of Wilmington, Delaware.

| Ingredient | % by Weight | Comments |
|---|---|---|
| 21 | | |
| Hydroxy propyl guar | 9.0 | Pourable in 1 |
| Boric acid | 0.25 | minute, strong |
| Galactose | 2.0 | gel. |
| .9% saline (NaCl) | 88.75 | pH = 6.5 |
| 22 | | |
| Hydroxy propyl quar | 9.0 | Mixable liquid |
| Boric acid | 0.5 | 1 minute, strong |
| Galactose* | 2.0 | gel. |
| .9% saline (NaCl) | 88.5 | pH = 6.4 |

*Other samples are made in which galactose is replaced by galactose pentasaccharide or mannose tetrasaccharide. Another sample is made with a tetrasaccharide containing both mannose and galactose in equal quantities.

| Ingredient | % by Weight | Comments |
|---|---|---|
| 23 | | |
| Hydroxypropyl guar | 9.0 | Gel formed in |
| Boric acid | 0.25 | less than 2 minutes, |
| Galactose | 3.0 | strong gel in |
| .9% saline (NaCl) | 87.75 | 5 minutes. |
| | | pH = 6.7 |
| 24 | | |
| Cationic guar | 9.0 | Homogeneous |
| Boric acid | 1.0 | liquid more than |
| Galactose | 1.0 | 3 minutes. |
| Mannose | 2.0 | pH = 6.3 |
| .9% saline (NaCl) | 87.0 | |
| 25 | | |
| Cationic guar | 9.0 | Pourable liquid |
| Boric acid | 1.0 | in 2 minutes. |
| Galactose | 3.0 | pH = 6.2 |
| .9% saline (NaCl) | 87.9 | |

-continued

| Ingredient | % by Weight | Comments |
|---|---|---|
| 26 | | |
| Cationic guar | 9.0 | Thickened more |
| Boric acid | 1.0 | slowly than |
| Mannose | 3.0 | example #25. |
| .9% saline (NaCl) | 87.0 | pH = 6.3 |
| 27 | | |
| Hydroxy propyl guar | 9.0 | Gel slightly |
| Boric acid | 0.5 | weaker, more |
| Lactose | 3.0 | elastic. |
| Water | 87.5 | pH = 7.1 |
| 28 | | |
| Hydroxy propyl guar | 9.0 | Clear translucent |
| Calcium chloride | 3.0 | gel, fair strength |
| Citric acid | 0.5 | and resilience. |
| Water | 87.5 | pH = 2.8 |
| 29 | | |
| Hydroxy propyl quar | 9.0 | White, very tough |
| Magnesium carbonate | 2.0 | elastic gel. |
| Citric acid | 0.25 | pH = 7.6 |
| Water | 88.75 | |
| 30 | | |
| Hydroxy propyl guar | 9.0 | Nice gel; fairly |
| Potassium antimony tartrate | 2.0 | weak. pH = 6.4 |
| Water | 89.0 | |
| 31 | | |
| Hydroxy propyl guar | 9.0 | Translucent gel. |
| Tyxor* | 2.0 | pH = 7.4 |
| Water | 89.0 | |

*An organic titanate, namely, titanium-ammonium lactate chelate, available from E.I. duPont of Wilmington, Delaware.

| Ingredient | % by Weight | Comments |
|---|---|---|
| 32 | | |
| Anionic guar | 12.0 | Much stronger |
| Boric acid | 0.63 | gel than |
| Borax | 4.37 | example #31. |
| Water | 83.0 | pH = 6.1 |
| 33 | | |
| Glucomannan (Konjak ®) | 12.0 | Long liquid phase, weak |
| Boric acid | 2.0 | gel. |
| Water | 86.0 | pH = 5.4 |
| 34 | | |
| Hydroxy propyl guar | 12.0 | Low cross-linking, |
| Borax | 0.5 | slimy gel. |
| Alum | 3.0 | pH = 4.1 |
| Water | 84.5 | |
| 35 | | |
| Hydroxy propyl guar | 12.0 | Gel had low |
| Calcium phosphate | 3.0 | cohesive strength. |
| Citric acid | 0.1 | pH = 6.8 |
| Water | 84.9 | |
| 36 | | |
| Guar (Supercol ®) | 8.0 | Gel forms rapidly and |
| Magnesium acetate | 2.0 | uniformly in about |
| Boric acid | 0.25 | 10 to 15 seconds. |
| Water | 89.7 | pH = 6.9 |
| 37 | | |
| Xanthan Gum | 10.0 | Rapid surface |
| Boric acid | 3.0 | hydration. |
| Water | 87.0 | |
| 38 | | |
| Xanthan gum | 3.0 | Lumps from rapid |
| Hydroxy propyl guar | 6.0 | surface hydration. |
| Boric acid | 0.25 | |

-continued

| Ingredient | % by Weight | Comments |
|---|---|---|
| Galactose | 2.0 | |
| Water | 88.75 | |
| 39 | | |
| Xanthan gum | 5.0 | Lumps from rapid |
| Locust bean gum | 5.0 | surface hydration. |
| Boric acid | 3.0 | |
| Water | 87.0 | |
| 40 | | |
| Potassium alginate | 3.1 | Stiff, gritty |
| Calcium sulfate | 3.1 | gel. |
| Trisodium phosphate | 1.6 | |
| Diatomaceous earth | 12.2 | |
| Water | 80.0 | |
| 41 | | |
| Sodium alginate | 3.55 | Stiff gel, not |
| Calcium sulfate | 3.55 | very elastic. |
| Sodium pyrophosphate | 0.71 | |
| Fine diatoinaceous earth | 21.28 | |
| Water | 70.91 | |
| 42 | | |
| Boric acid | 3.0 | Gel strength |
| Borax | 5.0 | moderate to low. |
| Guar (Supercol ®) | 3.0 | |
| Water | 89.0 | |
| 43 | | |
| Hydroxy propyl guar | 15.0 | Gel like example |
| Calcium sulfate | 3.5 | #36 except somewhat |
| Citric acid | 0.1 | greater cohesive |
| Water | 81.4 | strength. |

EXAMPLES CONTAINING BIOLOGICALLY ACTIVE SUBSTANCES

In the folloiwng examples, the symbol "D" indicates that the biologically active agent is in the dry constituent and "W" in the water.

44

A dressing is made as in Example #1 except that an antibiotic comprising 5 mg/g neomycin sulfate is added to the dry constituents to prevent and fight opportunistic infections. This medicament-containing dressing gel can be used for treating pathogenic wounds, stasis ulcers and chronic wounds. D

45

A dressing is made as in Example #2 except that an antibiotic comprising 400 Units/g of bacitracin is added to the dry ingredients to prevent and fight opportunistic infections. D

46

A dressing is made as in Example #3 except that 500 units/g of polymyxin B sulfate is included for preventing infections. D

47

A dressing is made as in Example #4 except that oxy tetracycline HCl is provided in the amount of 30 mg/g for infections. D

48

A dressing is made as in Example #5 except that 2.5 mg/g of gramacidin is included as an antibiotic for preventing and fighting infections. D

49

A wound dressing is prepared as in Example #6 except that a coagulant/astringent comprising alum in the amount of 75 mg/g is included to provide an emergency or battlefield dressing for reducing blood loss. W

50

A wound dressing is prepared as in Example #7 except that witch hazel in the amount of 200 mg/g is used as an astringent to provide an emergency or battlefield dressing for reducing blood loss. W

51

A wound dressing is prepared as in Example #8 with 2% to 10% in separate samples of povidone iodine is included in the composition as a disinfectant for treating pathogenic wounds, stasis ulcers and chronic wounds. D or W

52

A wound dressing is prepared as in Example #9 with ozone included in the amount of 50 mg/g as an oxygen base and a disinfectant for treating pathogenic wounds, stasis ulcers and chronic wounds. D

53

A wound dressing composition is prepared as in Example #10 with hydrogen peroxide used in the amount of 50 mg/g as a disinfectant for pathogenic wounds, stasis ulcers and chronic wounds. W

54

A wound dressing is prepared as in Example #11 containing a proteolytic enzyme comprising 20 units/g of collagenase to provide enzymatic debraidment of pathogenic wounds, stasis ulcers and chronic wounds. D

55

A wound dressing is prepared as in Example #12 containing a proteolytic enzyme comprising 10 units/g of streptokinase to provide enzymatic debraidment of pathogenic wounds, stasis ulcers and chronic wounds. D

56

A wound dressing is prepared as in Example #13 containing a proteolytic enzyme comprising 10 units/g of streptodornase to provide enzymatic debraidment. D

57

A wound dressing is prepared as in Example #14 including a diamine for reducing collagen cross-linking comprising 5 mg/g of putrescine. W

58

A wound dressing is prepared as in Example #15 including a polyamine for reducing collagen cross-linking comprising 10 mg/g of spermidine. W

59

A wound dressing is prepared as in Example #16 including a diamine for reducing collagen cross-linking comprising 15 mg/g of cadaverine. W

60

A wound dressing is prepared as in Example #17 including a growth factor comprising 40 units/g of platelet-derived growth factor to enhance natural healing processes and stimulate growth. D

61

A wound dressing is prepared as in Example #18 including a growth factor comprising 10 units/g of fibroblast growth factor to stimlate growth. D

62

A wound dressing is prepared as in Example #19 including a growth factor comprising 10 units/g of epidermal growth factor to stimulate growth. D

63

A wound dressing is prepared as in Example #20 including a growth factor comprising 10 units/g of transforming growth factor to stimulate growth. D

64

A wound dressing is prepared as in Example #21 including an immuno stimulator comprising 15 mg/g of L-arginine to stimulate the inflammatory phase of wound healing. D or W

65

A wound dressing is prepared as in Example #22 including an immuno stimulator comprising 5 mg/g of nitric oxide to stimulate wound healing. D or W

66

A wound dressing is prepared as in Example #23 including an immuno stimulator comprising 50 mg/g of quadrol to facilitate wound healing. W

67

A wound dressing is prepared as in Example #24 including an immunostimulator comprising 50 $\mu$g/g of muramyl dipeptide to enhance wound healing. D

68

A wound dressing is prepared as in Example #25 including an immunostimulator comprising 10 $\mu$g/g of macrophage activating factor to facilitate wound healing. D

69

A wound dressing is prepared as in Example #26 with 1 mg/g of hyaluronic acid added to facilitate healing of pathogenic wounds, stasis ulcers and chronic wounds. D or W

70

A wound dressing is prepared as in Example #36 with 20 mg/g of diamino polyethylene oxide (Jeffamine® EDR-148) for reducing collagen cross-linking. D or W

71

A wound dressing is prepared as in Example #1 with 5 mg/g morphine sulfate added as an analgesic for treating trauma wounds encountered in emergency or battlefield medicine. D or W

72

A wound dressing is prepared as in Example #6 with 1 mg/g of fentanyl citrate as an analgesic tranquilizer for treating emergency or battlefield wounds. D or W

73

A wound dressing is prepared as in Example #2 with 5 mg/g lidocaine hydrochloride as a local anesthetic for painful wounds. D or W

74

A wound dressing is prepared as in Example #7 with 10 mg/g of a 100:1 ratio of procaine hydrochloride and epinephrine as a local anesthetic which is also vasoconstrictive. This will lessen bleeding as well as aid in retention of the anesthetic to the site of need. D or W Many variations of the present invention within the scope of the appended claims will be apparent to those skilled in the art once the principles described herein are understood.

What is claimed is:

1. A pre-packaged wound dressing contained in a package for storing and mixing the dressing from which the dressing can be poured as a liquid and set up as a solid elastic body on the surface of a wound, said dressing comprising, about 3%–15% by weight of a natural or synthetic hydrocolloid polymer in dry particulate form contained in a compartment of said pouch, said polymer is a water soluble or water swellable hydrocolloid comprising a member selected from the group consisting of guar gum, locust bean gum, hydroxypropyl guar gum, polyglucomannan gum, cationic guar gum, anionic guar gum, alginate and xanthan gum, about 70%–95% by weight water contained in a second compartment of the package, the amount of said dry polymer relative to the amount of said water being effective to produce a liquid hydrocolloid dispersion of an initial viscosity which can be poured or spread onto a surface after said dry hydrocolloid polymer is mixed with said water and is capable of setting up to form a solid, said pre-packaged wound dressing including a biologically active substance for treating the wound, the water and the polymer being separated by a removable barrier that is a part of the package separating the polymer from the water to prevent communication between the dry hydrocolloid polymer and water for maintaining the hydrocolloid in the dry state, said dry hydrocolloid polymer, the biologically active substance and water being mixed together by rupturing or removing said barrier to form said liquid dispersion for being poured onto a wound or spread onto a wound after the water and polymer are mixed together, and after application to the wound, said dispersion solidifies to form a gel which is an elastic solid resting upon the wound, said elastic solid gel has a lower surface that corresponds to the shape of the wound surface, said elastic solid gel protects the wound, maintains the wound in a moist condition and maintains said biologically active substance in contact with the wound to promote healing or patient comfort.

2. The wound dressing of claim 1 wherein the biologically active substance comprises a coagulant and astringent comprising alum.

3. The wound dressing of claim 1 wherein the biologically active substance comprises an astringent comprising witch hazel.

4. The wound dressing of claim 1 wherein the biologically active substance comprises an antibiotic selected from the group consisting of neomycin sulfate, bacitracin, polymyxin-B sulfate, oxy tetracylcine hydrochloride, and gramacidin.

5. The wound dressing of claim 1 wherein the biologically active substance is selected from the group consisting of povidone iodine ozone, and hydrogen peroxide.

6. The wound dressing of claim 1 wherein the biologically active substance is a proteolytic enzyme selected from the group consisting of collagenase, streptokinase and streptodornase.

7. The wound dressing of claim 1 wherein the biologically active substance is a polyamine or diamine selected from the group consisting of spermadine, putrescine, cadaverine, cystamine, histadine and a synthetic diamine comprising a polyalkyleneoxide diamine.

8. The wound dressing of claim 1 wherein the biologically active substance is a growth factor selected from the group consisting of platelet-derived growth factor, fibroblast growth factor, epidermal growth factor, and transforming growth factor.

9. The wound dressing of claim 1 wherein the biologically active substance comprises an immunostimulator selected from the group consisting of L-arginine, nitric oxide, quadrol, muramyl dipeptide, and other macrophage activating factors.

10. The wound dressing of claim 1 wherein the biologically active substance comprises hyaluronic acid or hyaluronic acid fragment for promoting the healing of pathogenic wounds, stasis ulcers and chronic wounds.

11. The wound dressing of claim 1 wherein the biologically active substance comprises an analgesic or a narcotic.

12. The wound dressing of claim 1 wherein the biologically active substance comprises an anesthetic selected from the group consisting of lidocaine, procaine and epinephrine.

13. The wound dressing of claim 11 wherein the analgesic or narcotic is selected from the group consisting of morphine, heroin and fentanyl for treatment of pain.

14. The wound dressing of claim 1 wherein said liquid dispersion includes an agent for cross-linking said hydrocolloid polymer and said cross-linking agent comprises at least one member selected from the group consisting of galactose, organic titanate, boric acid, borax, mannose, an oligosaccharide containing either or both galactose or mannose, dihydroxy aluminum sodium carbonate, citric acid, and a soluble source of any of the cations of calcium, magnesium and aluminum.

* * * * *

UNITED STATES PATENT AND TRADEMARK OFFICE
CERTIFICATE OF CORRECTION

PATENT NO. : 5,804,213
DATED : Sep, 8, 1998
INVENTOR(S) : ROLF, David

It is certified that error appears in the above-indentified patent and that said Letters Patent is hereby corrected as shown below:

Col. 15, line 32 (claim 1, line 7), change "pouch" to ---package--- to agree with claim 1, lines 1 and 14 (Col. 15, lines 26 and 39).

Col. 16, line 19 (Claim 5, line 3), after "iodine" and before "ozone", insert ---,--- (a comma).

Signed and Sealed this

Twelfth Day of October, 1999

Q. TODD DICKINSON

Attest:

Attesting Officer

Acting Commissioner of Patents and Trademarks